US012678632B2

(12) United States Patent
Gries

(10) Patent No.: US 12,678,632 B2
(45) Date of Patent: *Jul. 14, 2026

(54) APPARATUS AND METHOD FOR GENERATING A MAGNETIC FIELD

(71) Applicant: ZIMMER MEDIZINSYSTEME GMBH, Neu-Ulm (DE)

(72) Inventor: Luka Gries, Neu-Ulm (DE)

(73) Assignee: ZIMMER MEDIZINSYSTEME GMBH, Neu-Ulm (DE)

( * ) Notice: Subject to any disclaimer, the term of this patent is extended or adjusted under 35 U.S.C. 154(b) by 1212 days.

This patent is subject to a terminal disclaimer.

(21) Appl. No.: 17/555,805

(22) Filed: Dec. 20, 2021

(65) Prior Publication Data

US 2023/0191145 A1     Jun. 22, 2023

(51) Int. Cl.
| | |
|---|---|
| *A61N 2/02* | (2006.01) |
| *A61N 1/375* | (2006.01) |
| *A61N 1/378* | (2006.01) |
| *H02M 3/315* | (2006.01) |
| *H02M 7/48* | (2007.01) |
| *H03K 3/00* | (2006.01) |

(52) U.S. Cl.
CPC ............... *A61N 2/02* (2013.01); *A61N 1/375* (2013.01); *A61N 1/3787* (2013.01); *H02M 3/315* (2013.01); *H02M 7/4815* (2021.05); *H03K 3/00* (2013.01)

(58) Field of Classification Search
CPC .......... A61N 2/00; A61N 2/002; A61N 2/004; A61N 2/006; A61N 2/008; A61N 2/02
See application file for complete search history.

*Primary Examiner* — Carrie R Dorna
(74) *Attorney, Agent, or Firm* — Nixon & Vanderhye PC

(57) ABSTRACT

A magnetic field for application to body tissue is generated via a first inductor. Connecting circuitry, including at least first and second branches, is provided between an electric storage device and the first inductor. A switch forming part of the first branch electrically connects the storage device to the first inductor enabling electrical current to flow through the first branch and the first inductor, thereby causing the first inductor to generate the field. The current flowing through the first branch represents a first direction of flow between the storage device and the first inductor. An electric component conducts current primarily in a forward direction. That component forms part of the second branch, enabling current to flow between the storage device and the first inductor through the second branch. The flow in the forward direction represents a second direction opposite the first. The first or second branch includes a second inductor.

19 Claims, 4 Drawing Sheets

APPARATUS AND METHOD FOR GENERATING A MAGNETIC FIELD

The present invention relates to an apparatus and a method for generating a magnetic field, in particular for application to (human or animal) body tissue.

The invention can in particular be used to generate an alternating magnetic field, i.e. a magnetic field whose magnetic field strength varies over time, and in particular a magnetic field whose magnetic field strength reverses its orientation over time. Such alternating magnetic fields can be used to generate a voltage in the body tissue, in particular so as to cause a neural reaction or a cellular physiological reaction in the body tissue, in particular so as to cause a muscle reaction in the body tissue. In some cases, the voltage can be sufficient to cause a therapeutic effect, or some other (desirable) effect in the body tissue, i.e. not necessarily a therapeutic effect, for example the strengthening of muscle tissue.

Various devices for generating an alternating magnetic field for application to body tissue are known in the art. FIG. 1 schematically shows a circuit diagram of a device for generating an alternating magnetic field known to the inventor (and not admitted as prior art). The circuit shown in FIG. 1 includes a capacitor 101 electrically connected, via two branches 105 and 106 of connecting circuitry, to an inductor 102. The capacitor 101 is also connected, via a switch 108, to a source of electrical energy, such as a voltage source 107. One terminal of each of the capacitor 101, inductor 102 and voltage source 107 is connected to ground (indicated by triangles towards the bottom of FIG. 1). Whilst switch 108 is shown in FIG. 1 as a separate circuit element, it can alternatively be integrated into, or form part of, voltage source 107.

A thyristor 103 forms part of the first branch 105, i.e. one terminal (in FIG. 1 the left-hand terminal, i.e. the anode) of the thyristor 103 is electrically connected to the capacitor 101. A second terminal (in FIG. 1 the right-hand terminal, i.e. the cathode) of the thyristor 103 is electrically connected to the inductor 102. A third terminal, the gate terminal of the thyristor, is electrically connected to suitable circuitry for "firing" the thyristor 103. Circuitry for firing the thyristor 103 is not shown in FIG. 1, but is known to those skilled in the art.

Similarly, a diode 104 forms part of the second branch 106, i.e. one terminal (in FIG. 1 the left-hand terminal, i.e. the cathode) of the diode 104 is electrically connected to the capacitor 101. A second terminal (in FIG. 1 the right-hand terminal, i.e. the anode) of the diode 104 is electrically connected to the inductor 102.

Accordingly, electrical current can flow between the capacitor 101 and the inductor 102 either via the first branch 105 or the second branch 106, depending on whether the thyristor 103 or the diode 104 is in a conductive state or "ON" state. In particular, the polarity of the thyristor 103 and the diode 104 is such that only one of these components is conductive at any one time. It will be appreciated that, even when the thyristor 103 or the diode 104 is in a non-conductive state, a small amount of electrical current may nevertheless flow through these components. For the purposes of the present application, the terms "conductive (state)" and "non-conductive (state)" and similar are preferably to be interpreted accordingly.

The direction of conventional current in an electrical circuit is defined as the direction in which positive charges flow. Negatively charged carriers, such as the electrons, therefore flow in the opposite direction of conventional current flow in an electrical circuit. In accordance with this convention, electrical current flowing from the capacitor 101 to the inductor 102 will (only) flow through the first branch 105 (assuming the thyristor 103 is in a conductive state), whereas electrical current flowing from the inductor 102 to the capacitor 101 will (only) flow through the second branch 106 (assuming the diode 104 is in a conductive state).

The inductor 102 can be brought into proximity with body tissue so that any magnetic field generated by inductor 102 is applied to the body tissue.

Typically, the operation of the device shown in FIG. 1 is as follows. The capacitor 101 is electrically charged by voltage source 107. To this end, switch 108 is closed at a suitable time so as to electrically connect voltage source 107 to capacitor 101. Switch 108 can be operated by suitable circuitry, which is again not shown in FIG. 1 but will be familiar to those skilled in the art. Once the capacitor 101 has been charged, either for a certain period of time or up to a certain voltage, switch 108 is opened. In the example shown in FIG. 1, the capacitor 101 will be charged such that the (in FIG. 1) upper terminal will be positive and the lower terminal will be negative. This is also indicated by the symbols "+" and "−" next to voltage source 107.

Initially, the electrical charge now stored in capacitor 101 will remain in capacitor 101 since the diode 104 is in a non-conductive state. Electrical current can (initially) also not flow from capacitor 101 to inductor 102 via the first branch 105, unless and until thyristor 103 is fired via its gate terminal.

Next, thyristor 103 is fired via its gate terminal. Current can now flow from capacitor 101 to inductor 102, thereby enabling inductor 102 to generate a magnetic field. As is known in the art, thyristor 103 remains in a conductive state even if the signal (gate current) which fired thyristor 103 is no longer present at its gate terminal.

While current flows from capacitor 101 through the first branch 105 and through inductor 102, the charge stored in capacitor 101 (and thus the voltage between the two terminals of capacitor 101) decreases. This decrease in voltage approximately follows a cosine shape, starting at an initial maximum value at the time when thyristor 103 is fired.

Due to energy losses in the circuit of FIG. 1, the voltage between the two terminals of capacitor 101 does not follow an exact cosine shape over time. Instead, the voltage more closely follows a cosine shape with a decaying amplitude, although even this may only be an approximation. The same applies to other voltages, currents or other variables which are described herein as (approximately) following a sine or cosine shape. This applies both to the circuit of FIG. 1 and to embodiments of the present invention. Accordingly, as used herein, the terms "cosine shape", "sine shape" and similar are to be understood to include (an approximation of) a cosine or sine shape with a decaying amplitude.

While the voltage between the two terminals of capacitor 101 decreases, the current through inductor 102 increases, starting at a value of zero and approximately following a sine shape, up to a maximum value. The current through inductor 102 reaches its maximum value substantially at the same time as the charge stored in capacitor 101 has dropped to zero. The period of time from the initial firing of thyristor 103 up to the point in time when the current through inductor 102 reaches its maximum value can be regarded as a quarter wave, or $\pi/2$.

At the time of $\pi/2$, a magnetic field generated by the current through inductor 102 is also at a maximum value, whilst the electrical energy stored in capacitor 101 is zero. In other words, the electrical energy that was initially stored in capacitor 101 has now been converted into magnetic energy, i.e. the magnetic field generated by the current through inductor 102. The energy is now stored in the magnetic field. As the magnetic field resists its decrease, current continues to flow through inductor 102 and through the first branch 105. The diode 104 is still in a non-conductive state. Accordingly, this continued current flow charges capacitor 101, but this time with opposite polarity compared with its initial state. As capacitor 101 is charged up to a negative maximum value (approximately corresponding to the initial maximum charge, but of opposite polarity), the current through inductor 102 and accordingly also the magnetic field decreases until, one half wave after initial firing of thyristor 103, or at the time of $\pi$, it has become zero. At this time, the charge (or voltage) of capacitor 101 has reached its maximum value of opposite polarity. Between $\pi/2$ and $\pi$, the voltage of capacitor 101 and current through inductor 102 continue to follow the approximated cosine and sine shapes, respectively.

Approximately at the end of this first half wave, thyristor 103 becomes non-conductive and diode 104 becomes conductive, in a or its forward direction. In the example shown in FIG. 1, this forward direction corresponds to a current direction from inductor 102 to capacitor 101. The process described above in connection with the first half wave is then effectively repeated during a second half wave, except that, at the time of $\pi$ (i.e. at a point in time at the end of the first half wave or at the beginning of the second half wave), the polarity of the voltage of capacitor 101 is the opposite of the initial polarity, and likewise the current direction through inductor 102 during the second half wave is the opposite of the current direction through inductor 102 during the first half wave. Further, the current between inductor 102 and capacitor 101 flows through the second branch 106, rather than through the first branch 105. The voltage of capacitor 101 and current through inductor 102 continue to follow, respectively, the (approximated) cosine and sine shapes which they started during the first half wave.

Eventually, after the second half wave, or at the time of $2\pi$, the system represented by the circuit shown in FIG. 1 has returned to its initial state, i.e. capacitor 101 is charged up to a maximum value and with the initial polarity, while the current through inductor 102 has returned to zero. Diode 104 becomes non-conductive at this stage. A complete cycle has been performed (two half waves). The process can then be repeated.

It is an object of the present invention to provide an apparatus and a method which offers more flexibility than the circuit described above in connection with FIG. 1.

Accordingly, the present invention provides an apparatus and a method in accordance with the independent claims. Further embodiments are set out in the dependent claims.

In a first aspect, the present invention provides an apparatus for generating a magnetic field for application to body tissue, the apparatus comprising:

an electric storage device for storing electrical energy;

a first inductor for generating a magnetic field for application to body tissue;

connecting circuitry between the electric storage device and the first inductor, wherein the connecting circuitry comprises at least a first branch and a second branch;

a switching device, wherein the switching device forms part of the first branch, wherein the switching device is configured to electrically connect the electric storage device to the first inductor in order to enable electrical current to flow through the first branch and through the first inductor, caused by the electrical energy stored by means of the electric storage device, thereby causing the first inductor to generate the magnetic field, wherein the electrical current flowing through the first branch represents a first current direction of current flow between the electric storage device and the first inductor;

an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction; and a second inductor, wherein the second inductor forms part of either the first branch or the second branch.

Accordingly, if, for example, the second inductor forms part of the second branch, current flowing in the second current direction would also flow through the second inductor—unless the second inductor is bypassed or short-circuited (which will be explained below).

In certain embodiments, the apparatus according to the first aspect can be constructed in a similar way to the circuit described in connection with FIG. 1. However, the addition of the second inductor in the first branch or the second branch constitutes a significant difference, not only in terms of the construction of the apparatus but also in terms of the operation of the apparatus, as will be explained below.

The electric storage device, in particular if a capacitor is used as electric storage device, together with the first inductor and the connecting circuitry can effectively be regarded as a resonant circuit (or LC circuit). However, whereas in a typical resonant circuit the electrical current would normally take the same path through the resonant circuit regardless of the direction in which it flows at any one time, in embodiments according to the first aspect, the electrical current would flow either through the first branch or the second branch, depending on the direction of current flow between the electric storage device and the first inductor. Further, after one complete cycle (two half waves) and assuming that the switching device has become non-conductive after the first half wave, the current flow stops until the switching device is operated (e.g. fired) again to allow current to flow through the first branch. Nevertheless, the behavior can be regarded as somewhat similar to that of a resonant circuit.

Assuming ideal components, the resonant frequency $\omega_0$ of a resonant circuit (in the following simply "frequency") is determined by the values of the inductance L and the capacitance C of the circuit, according to $$\omega_0 = \frac{1}{\sqrt{LC}}.$$

In an actual (non-ideal) circuit, other factors known to those skilled in the art will lead to slightly different results, but the above formula can still serve as an approximation, including for the purpose of embodiments of the present invention. Assuming again that a capacitor is used as electric storage device in the apparatus according to the first aspect of the invention, the capacitance C of the circuit is the same regardless of whether the electrical current flows through the first branch or the second branch. However, due to the additional second inductor in either the first branch or the second branch, the applicable inductance of the circuit depends on whether the current flows through the first branch or the second branch.

Applying this to a typical resonant circuit, this would mean that the frequency $\omega_0$ of the resonant circuit would depend on whether the current flows through the first branch or the second branch. In other words, the respective durations of the two half waves of a full cycle would be different. In embodiments of the first aspect of the present invention, the respective durations of the two half waves will also be different due to the addition of the second conductor in either the first branch or the second branch.

For the sake of simplicity, the system comprising the electric storage device, the first inductor and the first and/or second branch of the connecting circuitry, one of which will include the second inductor, will be referred to as a resonant circuit even though, strictly speaking, it does not necessarily constitute a resonant circuit. Similarly, a reference to the frequency of the resonant circuit is preferably intended to be understood not only to refer to an actual oscillation (in particular several consecutive oscillations), but also a reference to the duration of a half wave, or even more generally a reference to the rate of change (over time) of the electric current in the resonant circuit, a rate of change (over time) of a voltage at one of its components, or a rate of change (over time) of any other electrical property of the resonant circuit.

Suitable inductors for use as the first inductor and/or the second inductor are known in the art. They may in particular comprise at least one set of turns (of a wire) of any suitable shape, such as generally circular, hexagonal or rectangular turns. These turns may or may not be wound on a core.

The switching device of the apparatus according to the first aspect of the present invention may comprise a thyristor. Using a thyristor may be preferred over other switching devices since, once it has been fired, the thyristor remains in the conductive state even once the gate signal has been removed. Further, the thyristor changes into the non-conductive state once the polarity at its terminals (anode and cathode) is reversed.

However, other types of switching devices can be used instead of a ("normal") thyristor. For example, a gate turn-off (GTO-thyristor) can be used. This essentially has the same characteristics as a "normal" thyristor, but additionally it can be brought into the non-conductive state by applying a gate signal of the opposite polarity compared with the initial gate signal for firing the GTO-thyristor.

Further alternative switching devices include, without limitation, IGBT, FET or any other switching devices which can be switched on and off at appropriate times, in particular switched off after the first half wave.

If a switching device is used which actively needs to be switched off in order to revert to the non-conductive or "OFF" state, suitable switching circuitry may be provided. This can, for example, include a (micro-)controller, which may be programmed so as to switch the switching device on and/or off at desired points in time. As an alternative, or in addition, additional (analog) circuitry may be provided for switching the switching device off depending on a voltage which is present at a point in the first branch, in particular a voltage which is present at a terminal of the switching device which, as part of the first branch, is connected to the first inductor.

In the sense of the present invention, the term "electrical connection" is preferably intended to be understood to mean a connection enabling an electrical current to flow, in particular an electrical current of substantial magnitude. Such electric connection may be accomplished by a conductor such as a metallic wire, but may also involve semiconductor components in an ON-state. By way of contrast, the term "electrical connection" is preferably not intended to cover a semiconductor component in an OFF-state, even though an electrical current (such as a reverse leakage current in a diode or thyristor) may flow through such a semiconductor component when in the OFF-state. Any such reverse leakage current would typically be significantly smaller than an electrical current able to flow when the semiconductor component is in the ON-state. The term "electrically connect" is to be understood in a corresponding manner.

In embodiments of the first aspect of the present invention, various components can be used as the electric (or electronic) component or as part of an assembly of electric (or electronic) components in the second branch. This includes diodes, in particular those with a p-n junction or a metal-semiconductor junction (Schottky contact). More generally, it includes components which have a similar functionality as a diode, including rectifiers such as electrolytic rectifiers, mercury-arc rectifiers, plate rectifiers (metal rectifiers, in particular selenium rectifiers) and vacuum tube rectifiers (vacuum tube diodes).

The components listed in the preceding paragraph can be regarded as passive rectifiers, i.e. rectifiers which do not require any additional circuitry to influence the behavior of the rectifier. As an alternative, or in addition, active switching devices can be used, which can actively be switched by additional circuitry (which additional circuitry may be regarded as part of the assembly of electric or electronic components). Such circuitry may comprise analog circuitry and/or a microcontroller. Such (active) switching devices can be used instead of, for example, a diode in the second branch in any embodiments of the present invention.

In one embodiment, the apparatus further comprises circuitry to selectively bypass or short-circuit the second inductor in order to selectively vary an inductance of the branch of which the second inductor forms a part. Such circuitry to selectively bypass or short-circuit the second inductor may comprise an electrical connection between the two terminals of the second inductor, whereby this electrical connection comprises a further switching device so as to selectively interrupt or close this electrical connection. Assuming a relatively low-ohmic electrical connection is used to bypass or short-circuit the second inductor, electrical current through the branch of which the second inductor forms a part will (almost) exclusively flow through this bypass circuitry rather than through the second inductor (when the further switching device as part of this bypass circuitry is closed). Accordingly, if the bypass circuitry is closed, the inductance of the branch of which the second inductor forms a part is reduced when compared with a situation where the bypass circuitry is interrupted. This variance in inductance also has the effect of varying the frequency of the resonant circuit. In particular, when the current flows through the second inductor, the frequency of the resonant circuit is lower (i.e. the respective half wave then has a longer duration) than when the second inductor is bypassed. Further, when the current flows through the second inductor, the magnitude of the current through the resonant circuit is lower than when the second inductor is bypassed.

In one embodiment, an inductance of the second inductor is one of:

discretely variable; and substantially continuously variable.

Inductors of discretely variable or substantially continuously variable inductance are well known in the art. If the second inductor comprises a coil with a set of turns, the inductance can be varied discretely, by bypassing one or more (entire) turns or by bypassing a fraction of turns (for example three quarters of a turn or 5.375 turns). By using a variometer as the second inductor, the inductance can be varied substantially continuously. Other possible implementations of inductors of (continuously) variable inductance include inductors with a core, e.g. a coil with a set of turns wound around a core, whereby the core is (partially) introduced into, or withdrawn from, the coil.

In one embodiment, the apparatus further comprises one or more further inductors forming part of the branch of which the second inductor forms a part.

It is envisaged that the further inductors would be connected in series with the second inductor, although it would also be possible to connect them in parallel to the second inductor. Using two or more further inductors, it is also possible to use a combination of serial and parallel connections for the second and the further inductors.

In one embodiment, the apparatus further comprises circuitry to selectively bypass or short-circuit the second inductor and/or one or more of the one or more further inductors in order to selectively vary an inductance of the branch of which the second inductor forms a part.

The effect of bypassing or short-circuiting the second inductor has already been described above. Bypassing or short-circuiting one or more of the one or more further inductors, either as an alternative, or in addition, to bypassing or short-circuiting the second inductor has a corresponding effect, including the effect of varying the frequency of the resonant circuit and the effect of varying the magnitude of the current through the branch of which the second inductor forms a part.

In one embodiment, an inductance of the second inductor and/or of at least one of the one or more further inductors is one of:

discretely variable; and substantially continuously variable.

Again, inductors with a discretely variable inductance or a substantially continuously variable inductance have already been explained above in connection with the second inductor. This can apply in like manner to the one or more further inductors.

Using inductors with a discretely or substantially continuously variable inductance can be used in combination with circuitry for bypassing or short-circuiting the second inductor and/or one or more of the further inductors, but can also be used without such bypassing circuitry. By using inductors with a variable inductance in combination with bypassing circuitry, it is possible for the apparatus (the resonant circuit) to cover potentially a large variety of different frequencies, which may be variable in a discrete or substantially continuous manner.

In one embodiment, the inductances of the second inductor and of the one or more further inductors are chosen such that the inductance of the branch of which the second inductor forms a part is one of:

discretely variable; and substantially continuously variable from a minimum value up to a maximum value, wherein the minimum value corresponds to an inductance of the branch of which the second inductor forms a part when the second and the further inductors are bypassed or short-circuited; and wherein the maximum value corresponds to an inductance of the branch of which the second inductor forms a part when the second and the further inductors are not bypassed and not short-circuited and the inductance of the second inductor and/or of at least one of the one or more further inductors is at a maximum.

For example, if the second inductor and the one or more further inductors are connected in series, their inductances are added to result in a (total) inductance of the branch of which the second inductor forms a part. By selectively bypassing or short-circuiting the second and/or further inductors or by varying their individual inductances, the (total) inductance of the respective branch can be varied over a wide range.

In one embodiment, the first inductor comprises at least one set of turns, preferably at least one set of generally circular, hexagonal or rectangular turns, wherein the turns of the at least one set of turns are preferably arranged such that each turn generates a contribution towards the magnetic field when the electrical current flows through the first inductor, wherein the contributions generated by each turn are superimposed in a positive manner, wherein the first inductor is disposed within a casing connected to a conduit through which extends at least one cable for supplying electrical power to the at least one set of turns, and wherein the second inductor is not disposed within said casing.

According to this embodiment, the first inductor may for example be disposed in a casing made of plastics material, which may be separate from, and separately movable with respect to, a unit such as a housing or cabinet accommodating the electric storage device, the switching device and the electric component or assembly of electric components, as well as the first and second branch of the connecting circuitry. The casing which houses the first inductor can be connected to the cabinet by the conduit accommodating the cable for supplying electrical power to the first inductor. An arrangement in which the first inductor and the casing which houses the first inductor is connected to other components of the apparatus by means of a conduit such that the first inductor can be moved relative to such other components can advantageously be used to bring the first inductor in proximity with body tissue without moving these other components (e.g. a cabinet which houses these other components and which may be much larger and heavier than the first inductor and the casing accommodating the first inductor).

In one embodiment, the electric storage device comprises a pulse capacitor which can be charged by a charging circuit.

The charging circuit may form part of the apparatus, or may be provided as a separate device for connection to the apparatus of the first aspect of the invention. The charging circuit may in particular comprise a voltage source and a switch to selectively connect the voltage source to the capacitor.

In a second aspect, the present invention provides an apparatus for generating a magnetic field for application to body tissue, the apparatus comprising:

an electric storage device for storing electrical energy;

a first inductor for generating a magnetic field for application to body tissue;

connecting circuitry between the electric storage device and the first inductor, wherein the connecting circuitry comprises at least a first branch and a second branch;

a switching device, wherein the switching device forms part of the first branch, wherein the switching device is configured to electrically connect the electric storage device to the first inductor in order to enable electrical current to flow through the first branch and through the first inductor, caused by the electrical energy stored by means of the electric storage device, thereby causing the first inductor to generate the magnetic field, wherein the electrical current flowing through the first branch represents a first current direction of current flow between the electric storage device and the first inductor; and an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction;

wherein a total inductance of the first branch differs from a total inductance of the second branch by one of:

at least a factor of 1.5,
at least a factor of 2,
at least a factor of 5,
at least a factor of 10,
at least a factor of 50,
at least a factor of 100,
at least a factor of 500,
at least a factor of 1000,
at least a factor of 2000,
at least a factor of 5000,
at least a factor of 10000.

Pursuant to the second aspect, the inventor has recognized that the various components of the apparatus are not "ideal" components in the electrical sense. For example, the individual components such as the electric storage device, the first inductor, the switching device and the electric components or assembly of electric components forming part of the second branch, as well as the connecting circuitry would typically have one or more of a parasitic resistance, capacitance and inductance. In particular, both the first branch and the second branch will have a non-zero inductance. However, by ensuring that the inductance of the first branch differs from the inductance of the second branch (at least by one of the factors stated above, the frequency respectively associated with the first and the second branch (each in combination with the electric storage device and the first inductor) will also be different, in particular significantly different.

The difference in inductance between the first branch and the second branch can be achieved in particular by including a second inductor (and potentially further inductors) in one of the branches, as has been explained in connection with the first aspect of the invention.

In a third aspect, the present invention provides a method of generating a magnetic field, the method comprising:

providing an apparatus according to the first aspect;
storing electrical energy in the electric storage device;
switching the switching device so as to electrically connect the electric storage device to the first inductor and thereby enabling electrical current to flow through the first branch and through the first inductor, caused by the electrical energy stored by means of the electric storage device, thereby causing the first inductor to generate the magnetic field; and enabling electrical current to flow between the electric storage device and the first inductor through the second branch via said electric component or assembly of electric components.

In one embodiment, the apparatus used in the third aspect is operated in a pulsed manner, wherein the electrical current flowing through the first branch represents a first half pulse and wherein the electrical current flowing through the second branch represents a second half pulse, wherein a duration of the second half pulse is different from a duration of the first half pulse.

The difference in duration of the two half pulses stems from the difference in inductance of the first branch and the second branch, in particular due to the second (and any further) inductors forming part of one of the branches.

In one embodiment, the method further comprises selectively bypassing or short-circuiting the second inductor or varying an inductance of the second inductor, thereby selectively varying an inductance of the branch of which the second inductor forms a part.

The bypassing or short-circuiting of the second inductor, as well as the varying of the inductance of the second inductor has already been explained in connection with the first aspect of the present invention.

In one embodiment, selectively bypassing or short-circuiting the second inductor or varying the inductance of the second inductor comprises selectively bypassing or short-circuiting the second inductor or varying the inductance of the second inductor one of:

during the first half pulse,
during the second half pulse, and
between the first half pulse and the second half pulse.

Suitable (switching) circuitry can be used for actively bypassing or for short-circuiting the second inductor or for varying the inductance of the second inductor. Depending on when this bypassing, short-circuiting or varying takes place, different effects can be achieved: if done during the first half pulse (and assuming that the second inductor forms part of the first branch), the frequency of the resonant circuit is changed during the first half pulse, and accordingly the duration of the first half pulse is changed part-way through the first half pulse. Similarly, if done during the second half pulse (and assuming that the second inductor forms part of the second branch), the frequency of the resonant circuit is changed during the second half pulse, and accordingly the duration of the second half pulse is changed part-way through the second half pulse. In both cases, the signal (e.g. the current through the first inductor) changes its shape at the time when the second inductor is bypassed or short-circuited or its inductance is varied. That is, it does not continue to follow the same shape of the half pulse of the (approximated) sinewave that it followed initially, but instead continues along the shape of a different (approximated) sinewave (of a different pulse duration). If the second inductor is bypassed or short-circuited or its inductance is varied between the first half pulse and the second half pulse, the shape of each half pulse (approximately) resembles a half pulse of a sinewave. However, the duration and amplitude of the two half pulses will be different. The same applies, mutatis mutandis, if the second inductor is bypassed or short-circuited or its inductance is varied between one (full) pulse and the next (full) pulse.

A corresponding effect can be achieved by initially bypassing or short-circuiting the second inductor and interrupting the bypass or short-circuit either during the first half pulse, during the second half pulse, between the two half pulses or between one (full) pulse and the next (full) pulse.

In one embodiment, the method further comprises bringing the first inductor into proximity with body tissue, or bringing the body tissue into proximity with the first inductor, so that the magnetic field is present in said body tissue.

This may in particular be used for therapeutic purposes, but can also be used for non-therapeutic purposes.

As the second inductor influences the frequency of the resonant circuit and the magnitude of the current through the first inductor, the second inductor also has an influence on the magnetic field generated by the first inductor, which can be used to achieve particular effects in the body tissue.

According to this embodiment, bringing the first inductor into proximity with body tissue can for example be accomplished by moving the first inductor, sometimes also called applicator coil, towards body tissue, or by moving it along the skin of a person or animal. An example of bringing the body tissue into proximity with the first inductor can involve the use of the first inductor in a (temporarily) fixed position, and a person or animal approaching the first inductor. Such a first inductor in a fixed position may for example be attached to, or integrated into, a chair or similar.

Also, it is possible first to bring the first inductor into proximity with body tissue (or to bring the body tissue into proximity with the first inductor) and then to generate the magnetic field, or vice versa.

The distance between the first inductor and the body tissue may for example be a few millimeters or centimeters, although larger distances (such as several tens of centimeters) may also be considered.

In one embodiment, the method further comprises varying the magnetic field in the body tissue so as to generate a voltage in the body tissue or to cause a movement of charges in the body tissue.

As the magnetic field in the body tissue varies with the current through the first inductor, the voltage is generated (or the movement of charges is caused) in the body tissue through the magnetic field.

In one embodiment, the generated voltage (or the movement of charges) in the body tissue is sufficient to cause a neural reaction or a cellular physiological reaction, in particular a muscle reaction in the body tissue, wherein preferably the voltage is sufficient to cause a therapeutic effect.

A variety of effects can be achieved in a targeted manner using the apparatus of the first aspect or the method of the third aspect, in particular by suitable choice of the second inductor and, if applicable, bypassing or short-circuiting the second inductor or varying the inductance.

In a fourth aspect, the present invention provides an apparatus for use with a first inductor for generating a magnetic field for application to body tissue, the apparatus comprising:

an electric storage device for storing electrical energy;

a terminal for connection to the first inductor for generating a magnetic field for application to body tissue;

connecting circuitry between the electric storage device and said terminal, wherein the connecting circuitry comprises at least a first branch and a second branch;

a switching device, wherein the switching device forms part of the first branch, wherein the switching device is configured to electrically connect the electric storage device to said terminal so as to enable electrical current to flow through the first branch and through the first inductor via said terminal when the first inductor is connected to the apparatus via said terminal, caused by the electrical energy stored by means of the electric storage device, thereby causing the first inductor to generate the magnetic field, wherein the electrical current flowing through the first branch represents a first current direction of current flow between the electric storage device and said terminal;

an electric component or assembly of electric components, preferably an electronic component or assembly of electronic components, that conducts, or is arranged to conduct, electrical current primarily in a forward direction, wherein said electric component or assembly of electric components forms part of the second branch so as to enable electrical current to flow between the electric storage device and the first inductor through the second branch via said terminal when the first inductor is connected to the apparatus via said terminal, wherein the current flow in the forward direction represents a second current direction of current flow between the electric storage device and the first inductor, the second current direction being opposite the first current direction; and a second inductor, wherein the second inductor forms part of either the first branch or the second branch.

The apparatus of the fourth aspect is similar to the apparatus of the first aspect. However, in contrast to the first aspect, the first inductor mentioned in connection with the fourth aspect does not form part of the apparatus of the fourth aspect. Instead, the apparatus of the fourth aspect has a terminal (such as an electric socket or similar) for connection to the first inductor. Accordingly, a number of (different) inductors, for example inductors having different shapes, inductances or other characteristics, can selectively be connected to the apparatus of the fourth aspect and used as the first inductor.

In any embodiments described herein, the first inductor and/or an applicator in which the first inductor is accommodated may, for example, be of a generally flat construction so that the first inductor and/or applicator may be applied to a body portion substantially from one side. Other shapes or construction types are also possible, for example that of a hollow cylinder or similar, so that the windings of the first inductor may surround the body portion, i.e. the first inductor or applicator may be applied over the body portion, or the body portion (e.g. arm, leg, torso) may be introduced into, or pass through, the inductor or applicator.

Further, the construction of any, some or all of the inductors discussed in the present application, in particular of the first inductor, is not limited to any particular design. In particular, any, some or all of the inductors, in particular the first inductor, may, for example, be constructed in such a way that each (360°) turn or winding of the respective inductor comprises, or consists of, one solid (and substantially rigid) piece of conductive material (e.g. copper), rather than several strands running in parallel. Alternatively, each (360°) turn or winding of the respective inductor may comprise, or consist of, a small number (such as no more than 2, or no more than 3, or no more than 4, or no more than 5) of solid (and substantially rigid) pieces of conductive material (e.g. copper), insulated from one another. In other embodiments, any, some or all of the inductors, in particular the first inductor, may, for example, be constructed from litz-wire, wherein each wire is insulated separately, and may in particular comprise a litz-wire coil. This may reduce eddy currents in the inductor.

The various embodiments and advantages described above in connection with any one aspect of the present invention similarly apply to the other aspects of the invention. Each feature disclosed and/or illustrated in the present specification may be incorporated in the invention, whether alone or in combination with any other feature disclosed or illustrated herein, unless such combination is explicitly excluded or technically impossible.

Some embodiments of the invention will now be described by way of example only and with reference to the accompanying drawings, in which:

FIG. 1 schematically shows a circuit diagram of a device for generating an alternating magnetic field known to the inventor (and not admitted as prior art).

FIG. 2 schematically shows a circuit diagram of an apparatus for generating a magnetic field in accordance with an embodiment of the present invention.

FIG. 3 schematically shows a circuit diagram of an apparatus for generating a magnetic field in accordance with an embodiment of the present invention.

FIG. 4 schematically shows a circuit diagram of an apparatus for generating a magnetic field in accordance with an embodiment of the present invention.

FIG. 5 schematically shows an apparatus for generating a magnetic field in accordance with an embodiment of the present invention.

Figure 1:
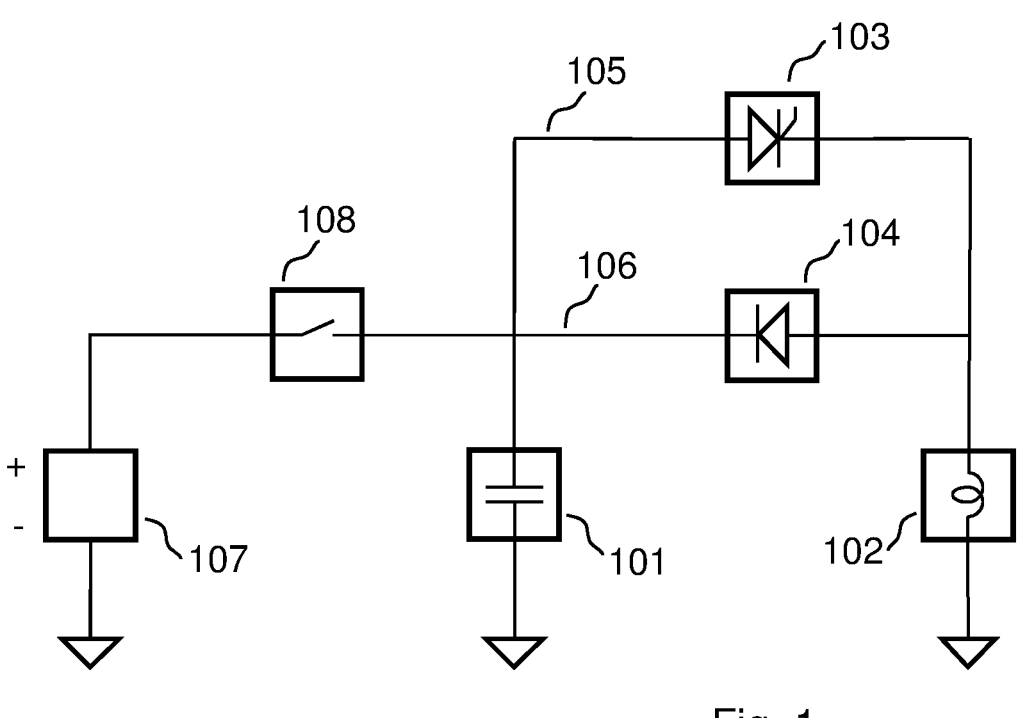
Figure 2:
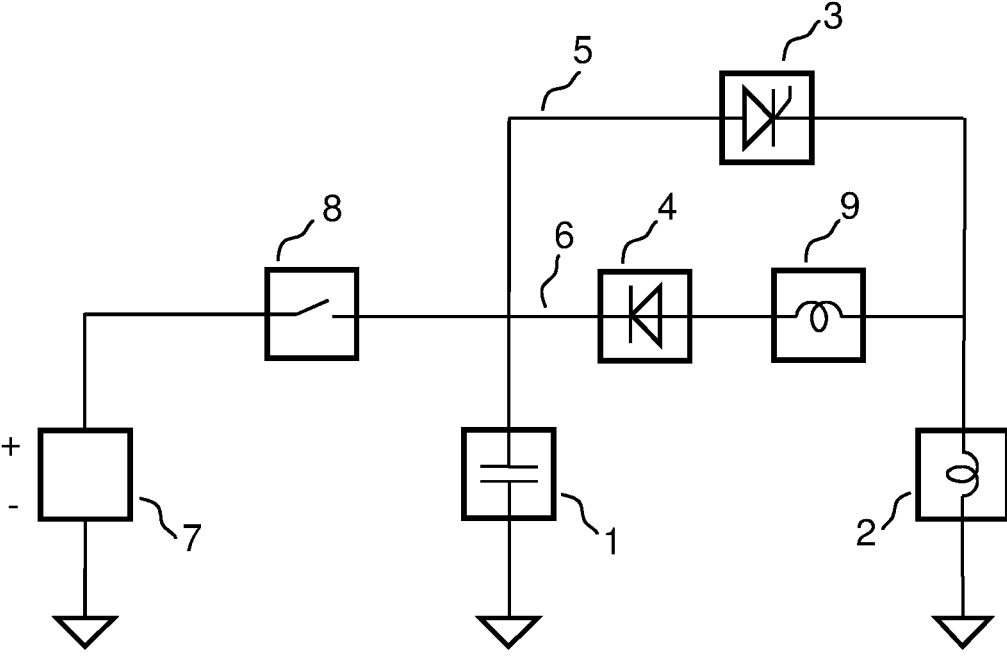

FIG. 2 schematically shows a circuit diagram of an apparatus for generating a magnetic field in accordance with an embodiment of the present invention. The circuit diagram shown in FIG. 2 is similar to that shown in FIG. 1. The above explanations regarding the device shown in FIG. 1 therefore also apply to the circuit diagram shown in FIG. 2 and will not be repeated here. Elements shown in FIG. 2 corresponding to elements shown in FIG. 1 carry the same reference signs reduced by 100. However, it should be noted that various modifications are possible. For example, while in many embodiments the source of electrical energy 7 (e.g. a voltage source 7) may be mains powered, it can alternatively be non-mains powered and may, for example, comprise a battery or a battery arrangement comprising one or more batteries. Switching device 3 is shown as a thyristor, but other switching devices can be used, as has been explained above. Electric component 4 in the second branch 6 is shown as a diode, but other electric components or an assembly of electric components, in particular electronic components or an assembly of electronic components, can be used, as has been explained above. However, in the interest of a compact explanation, the description of the circuit diagram shown in FIG. 2 will proceed using the same terminology as has been used in connection with FIG. 1.

Further, a charging circuit comprising a source of electrical energy 7 and a switching device 8 is shown for better understanding, although the invention includes embodiments without such a charging circuit (but which can be used together with such a charging circuit, in particular which can be electrically connected to such a charging circuit).

The second branch 6 shown in FIG. 2 includes a second inductor 9 connected in series with diode 4. Electrical current flowing between the first inductor 2 and the capacitor 1 through the second branch 6 will also flow through the second inductor 9. Considering the current flow through the first inductor 2 and the second branch 6 and the capacitor 1, the second inductor 9 is effectively connected in series with the first inductor 2. No such additional inductor forms part of the first branch 5, and therefore the inductance of the second branch 6 is higher than the inductance of the first branch 5, in particular significantly higher. Therefore, when considering the capacitor 1, the first inductor 2 and either the first branch 5 or the second branch 6 as a resonant circuit, it can be seen that the frequency of the resonant circuit including the second branch 6 is (significantly) lower than the frequency of the resonant circuit including the first branch 5.

Figure 3:
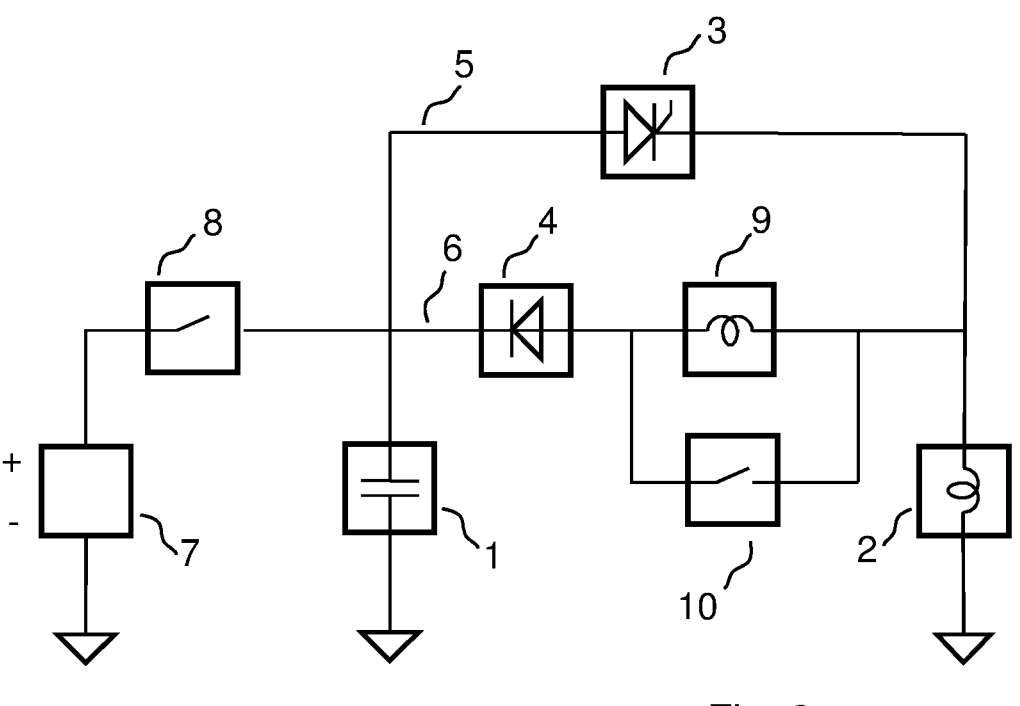

FIG. 3 schematically shows a circuit diagram of an apparatus for generating a magnetic field in accordance with an embodiment of the present invention. The embodiment shown in FIG. 3 is similar to that shown in FIG. 2, and the same explanations provided in connection with FIG. 2 also apply to the embodiment shown in FIG. 3. Like components carry like reference signs. FIG. 3 additionally shows circuitry for bypassing or short-circuiting the second inductor 9. This bypassing circuitry is connected to the two terminals of the second inductor 9 and includes a further switching device 10 to enable the bypassing circuitry to selectively bypass the second inductor 9. When the further switching device 10 is closed, any electrical current flowing through the second branch 6 will predominantly or (almost) exclusively flow through the bypassing circuitry, thereby substantially preventing current from flowing through the second inductor 9. In this way, the total inductance of the second branch 6 can be changed between a maximum value (further switching device 10 open) and a minimum value (further switching device 10 closed). When the further switching device 10 is closed, the inductance of the second branch 6 may be similar to the inductance of the first branch 5.

Figure 4:
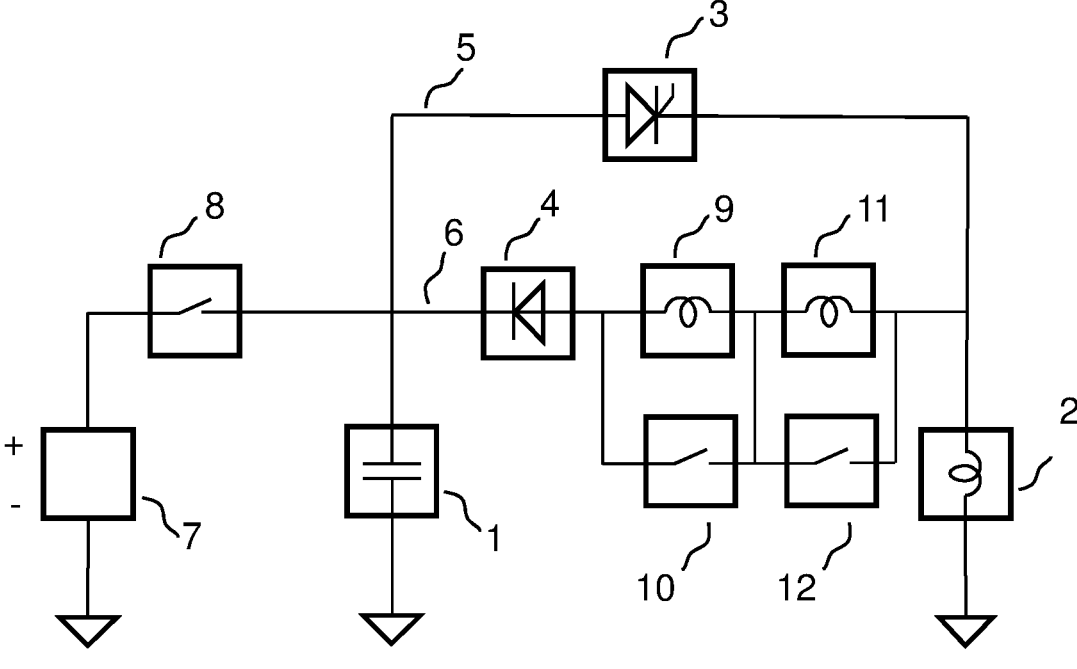

FIG. 4 schematically shows a circuit diagram of an apparatus for generating a magnetic field in accordance with an embodiment of the present invention. The embodiment shown in FIG. 4 is similar to that shown in FIG. 3, and the same explanations provided in connection with FIG. 3 also apply to the embodiment shown in FIG. 4. Like components carry like reference signs. FIG. 4 additionally shows a further inductor 11 forming part of the second branch 6 and connected in series with the second inductor 9 (and the diode 4). The circuit diagram shown in FIG. 4 additionally includes further circuitry for bypassing or short-circuiting the further inductor 11. This further bypassing circuitry is connected to the two terminals of the further inductor 11 and includes a further switching device 12 to enable the further bypassing circuitry to selectively bypass the further inductor 11. When the further switching device 12 is closed (or conductive), any electrical current flowing through the second branch 6 will predominantly or (almost) exclusively flow through the further bypassing circuitry, thereby substantially preventing current from flowing through the further inductor 11. In this way, the total inductance of the second branch 6 can be varied.

Using the two further switching devices 10 and 12, the total inductance of the second branch 6 can be changed between a maximum value (both further switching devices 10 and 12 open or non-conductive) and a minimum value (both further switching devices 10 and 12 closed or conductive). When both further switching devices 10 and 12 are closed, the inductance of the second branch 6 may be similar to the inductance of the first branch 5. When only one of the further switching devices 10 and 12 is closed and the other is open, only one of the second inductor 9 and the further inductor 11 will be bypassed, and accordingly the total inductance of the second branch 6 will be at an intermediate value between the minimum value and the maximum value.

According to a variant of the embodiment shown in FIG. 4, the bypassing circuitry associated with either the second inductor 9 or the further inductor 11 can be omitted. The respective inductor will therefore be permanently connected in series with the diode 4, whereas the other of the second inductor 9 and the further inductor 11 (the bypassing circuitry of which is not omitted) can selectively be bypassed using its associated bypassing circuitry.

According to a further variant of the embodiment shown in FIG. 4, yet further inductors can be added to the second branch 6 in series with the diode 4, the second inductor 9 and the further inductor 11. Each of these yet further inductors may or may not have their associated bypassing circuitry similar to the bypassing circuitry associated with the second inductor 9 and the further inductor 11.

According to a variant of any of the embodiments described with reference to FIGS. 2, 3 and 4 (or any of the variants already explained above), any one or more of the second inductor 9, the further inductor 11 and the yet further inductors (if provided) may comprise inductors with a variable inductance. Details of inductors with a variable inductance have already been explained above.

In a further development of this variant, only one of the inductors in the second branch 6 is of variable inductance, for example the second inductor 9. Nevertheless, by suitable choice of the (maximum) inductance of the second inductor 9 and of the inductance of the further inductors in the second branch 6, the total inductance of the second branch 6 can be adjustable over a relatively wide range, in particular in small steps or (substantially) continuously. In this further development, each of the further inductors is provided with associated bypassing circuitry. The second inductor 9 of variable inductance may or may not be provided with associated bypassing circuitry. If the inductances of the second inductor (L2) and of the further inductors (L3, L4, L5, L6 etc.) are chosen according to a ratio of 1:1:2:4:8 etc., the lowest value of total inductance of the second branch 6 can be achieved if the third inductor (of inductance L3) and any further inductors (of inductance L4, L5, L6 etc.) are bypassed and the variable inductance (L2) of the second inductor 9 is adjusted to a minimum value L2min. By adjusting the variable inductance L2 of the second inductor 9 over its adjustable range to a maximum value L2max, the total inductance of the second branch 6 can be adjusted from L2min to L2max. If (only) the third inductor is not bypassed (and the fourth and any further inductors are bypassed), the total inductance of the second branch 6 can be adjusted from L3+L2min to L3+L2max by adjusting the variable inductance L2 of the second inductor 9 over its adjustable range. If (only) the fourth inductor is not bypassed (and the third, fifth and any further inductors are bypassed), the total inductance of the second branch 6 can be adjusted from L4+L2min to L4+L2max. The next adjustable range of the total inductance can be achieved by not bypassing the third and fourth inductor and bypassing the fifth and any further inductors, and so on. If the relative inductances of the second inductor and of the further inductors are chosen according to the above ratio, and further assuming that the variable inductance L2 of the second inductor 9 can be adjusted down to substantially zero (L2min=0), the total inductance of the second branch 6 can be adjusted (in discrete steps or substantially continuously) from substantially 0 to a maximum total inductance corresponding to the sum of all inductances of the inductors forming part of the second branch 6, i.e. L2max+L3+L4+L5 etc.

According to a further variant, which can be based on any of the above embodiments or variants, the second and/or any further inductors (together with any associated bypassing circuitry) are included in the first branch 5, rather than the second branch 6.

Figures 5, 6:
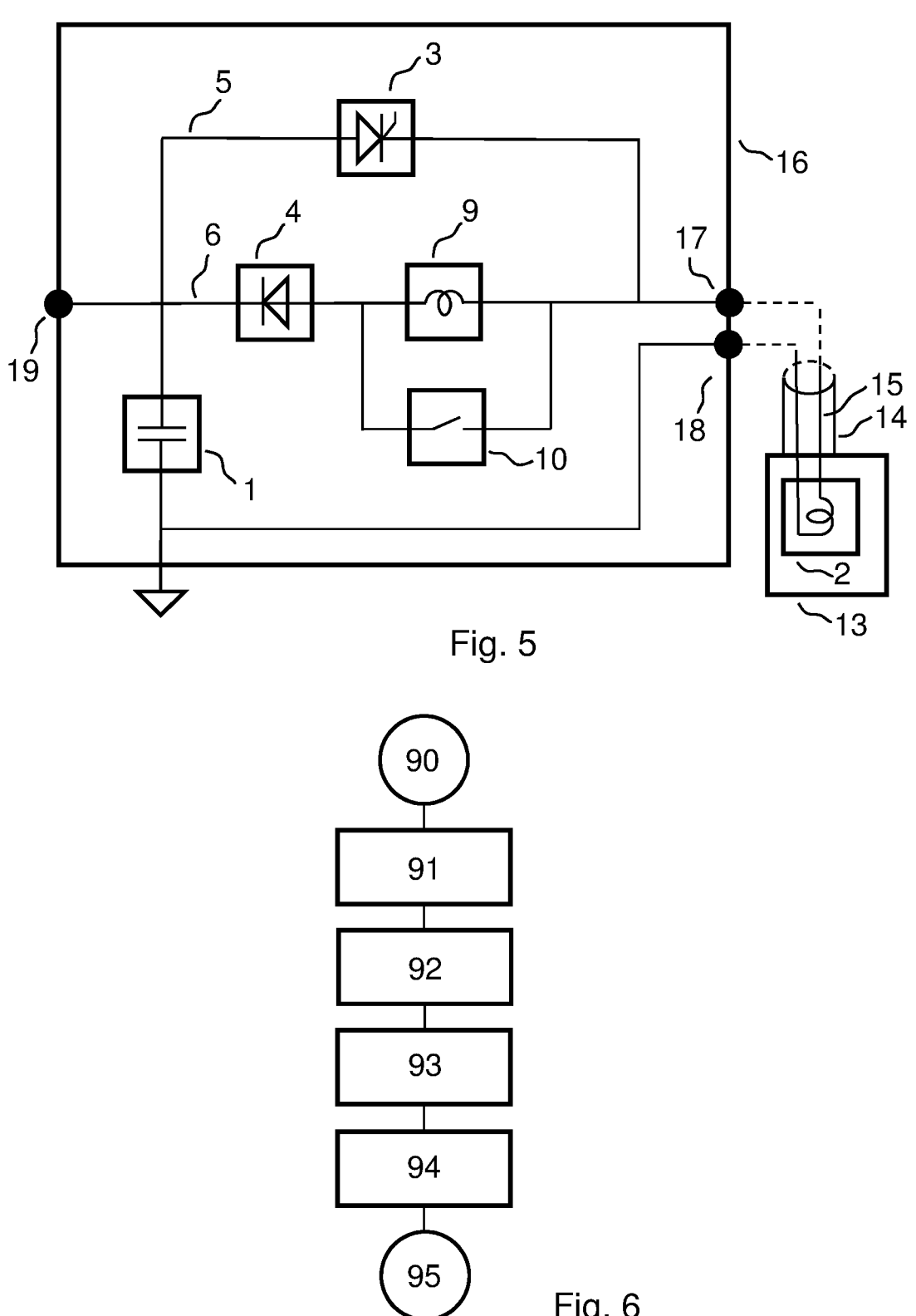
FIG. 6 shows a flowchart illustrating a method in accordance with an embodiment of the present invention.

FIG. 5 schematically shows an apparatus for generating a magnetic field in accordance with an embodiment of the present invention. This is closely based on the embodiment shown in FIG. 3. However, the charging circuit shown in FIG. 3 is not shown in FIG. 5.

Instead, FIG. 5 shows the capacitor 1 and the first and second branches 5 and 6 incorporated in a housing or cabinet 16 (electrically insulated from electric components and circuitry accommodated by cabinet 16). A terminal 19 for connection to an external charging circuit is provided on the cabinet 16 for the purpose of charging the capacitor 1. In a variant, the charging circuit, for example as shown in FIG. 3, can also be incorporated in the cabinet 16.

Cabinet 16 is provided with two further terminals, 17 and 18. Terminal 17 is connected to the first branch 5 and second branch 6, whereas terminal 18 is connected to ground. In the embodiment shown in FIG. 5, terminal 18 is connected to the ground connection for the capacitor 1 via a line running within the cabinet 16.

FIG. 5 shows the first inductor 2 as a separate entity from cabinet 16 and its contents. The first inductor 2 is accommodated in a casing 13, which is attached to a conduit 14. Conduit 14 accommodates a cable 15, which is electrically connected to the first inductor 2, in particular to at least one set of turns of inductor 2, and which can be connected to the terminal 17 as indicated by a dashed line. In the embodiment shown in FIG. 5, the inductor 2 can also be connected, via a second cable, to the ground terminal 18 on cabinet 16.

As a variant of the embodiment shown in FIG. 5, the second inductor 2 could be connected to ground via a separate line, i.e. not via the cabinet 16. In this case, the ground terminal 18 and the internal connection to ground could be omitted.

In further variants, features of the embodiment shown in FIG. 5 can be combined with the embodiments shown in FIGS. 2 and 4 or any variants described herein. Further, in any of the above embodiments or variants, any or all connections to ground could be omitted and replaced by an electrical connection between the different portions of the circuit. For example, in FIG. 2, the three connections to ground (triangles towards the bottom of the figure) could be replaced by an interconnection so that the (in FIG. 2 lower side of) capacitor 1, first inductor 2 and voltage source 7 are electrically connected.

In any of the above embodiments or variants, the polarities of the individual components can be reversed so that, for example, the negative terminal of the voltage source 7 is connected, via the switching device 8, to the first branch 5, second branch 6 and capacitor 1. The polarities of the thyristor 3 and the diode 4 would then also be reversed. Further, as has already been mentioned, the inventor has appreciated that the components and interconnections described in connection with the present invention are not "ideal" in the electrical sense. Enabled by the present disclosure, one skilled in the art will be able to make appropriate adjustments to allow for this. This applies in particular, but not exclusively, to the variant described above in which inductors having inductances according to a ratio of 1:1:2:4:8 etc. can be used. Appropriate adjustments can be made so as to take parasitic inductances into account, for example.

FIG. 6 shows a flowchart illustrating a method in accordance with an embodiment of the present invention. After the start 90 of the method, any one of the apparatuses described above is provided (91). Electrical energy is then (92) stored in the electric storage device, in particular the capacitor 1. Thereafter, the switching device 3, in particular the thyristor 3, is switched (93) into a conductive or "ON" state so as to electrically connect the electric storage device 1 to the first inductor 2. This enables electrical current to flow through the first branch 5 and through the first inductor 2, caused by the electrical energy stored by the electric storage device 1, thereby causing the first inductor 2 to generate a magnetic field. This current flow may represent a first half pulse or half wave. At the end of the first half pulse or half wave, electrical current is then enabled (94) to flow between the electric storage device 1 and the first inductor 2 through the second branch 6 via the electric component or assembly of electric components 4. This current flow may represent a second half pulse or half wave. Assuming the second and any further inductors 9, 11 are not bypassed or short-circuited, electrical current will also flow through the second and any further inductors 9, 11 during this second half pulse or half wave. At the end of the second half pulse or half wave, the method may end (95). Alternatively, the method or part thereof may be repeated. In particular, the switching device or thyristor 3 can again be switched (93) into the conductive or "ON" state etc. Electrical energy may also again be stored (92) in the electric storage device 1. In particular, the capacitor 1 may be recharged to its initial charging state, e.g. to compensate for dissipation of electrical energy in the apparatus.

Figure 7:
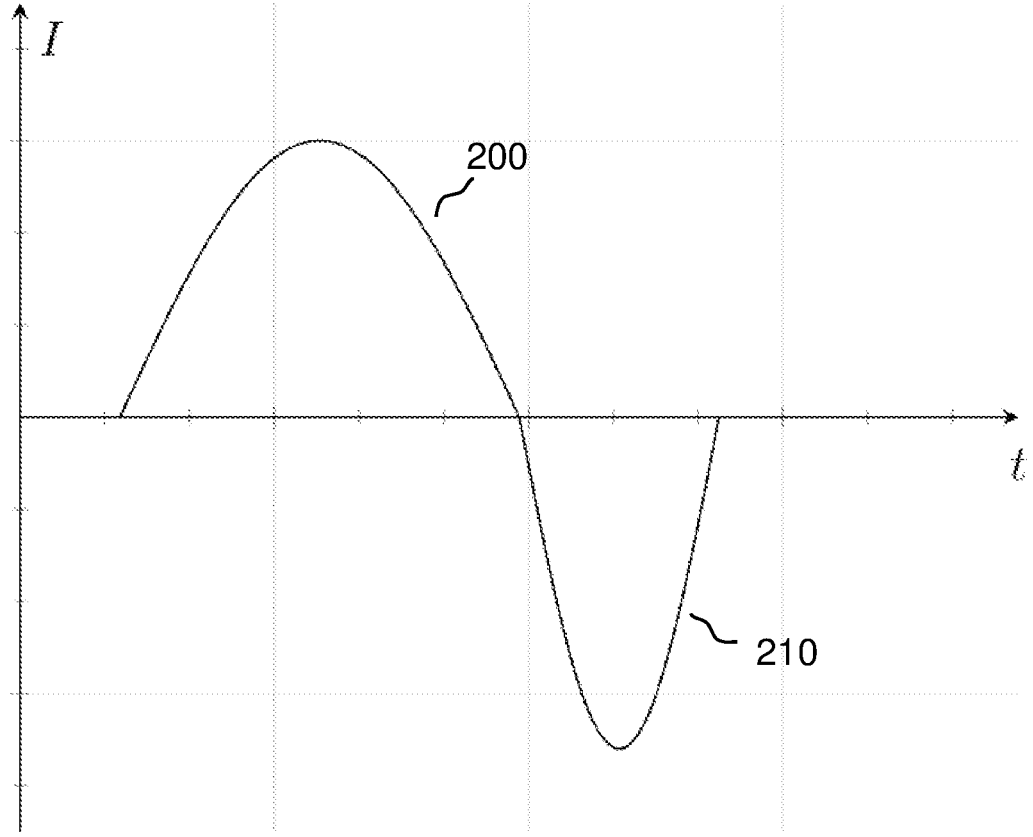
FIG. 7 shows a diagram in which the current through the first inductor is plotted over time, in accordance with an embodiment of the present invention.

FIG. 7 shows a diagram in which the current through the first inductor 2 is plotted over time, in accordance with an embodiment of the present invention. A circuit which might result in the diagram of FIG. 7 could be the circuit shown in FIG. 2, except that the second inductor 9 would be located in the first branch 5 (in series with the switching device 3), rather than the second branch 6. The first half pulse shown in FIG. 7 exhibits a slower rise and fall of the current through the first inductor 2 than the second half pulse. This is due to the higher total inductance during the first half pulse (total inductance=inductance of first inductor 2 of second inductor 9) when compared with the total inductance during the second half pulse (total inductance=inductance of first inductor 2).

While at least one example embodiment of the present invention has been described above, it has to be noted that a great number of variations thereto exist. Furthermore, it is to be appreciated that the described example embodiments only illustrate non-limiting examples of how the present invention can be implemented and that it is not intended to limit the scope, the application or the configuration of the apparatuses and methods described herein. Rather, the preceding description will provide the person skilled in the art with instructions for implementing at least one example embodiment of the invention, whereby it has to be understood that various changes in the functionality and the arrangement of the elements of the example embodiment can be made without deviating from the subject-matter defined by the appended claims and their legal equivalents.

LIST OF REFERENCE SIGNS

1 electric storage device, capacitor
2 first inductor, set of turns
3 switching device, thyristor
4 electric component or assembly of electric components, diode
5 first branch (of connecting circuitry)
6 second branch (of connecting circuitry)
7 source of electrical energy, voltage source
8 switch, switching device, switching circuitry
9 second inductor

10 bypass circuitry
11 further inductor
12 further bypass circuitry
13 casing
14 conduit
15 cable
16 housing, cabinet
17-19 terminals
90-95 method steps
101 capacitor
102 inductor
103 thyristor
104 diode
105 first branch
106 second branch
107 voltage source
108 switch
200 first half pulse
210 second half pulse

The invention claimed is:

1. An apparatus for generating a magnetic field for application to body tissue, the apparatus comprising:
   an electric storage device configured to store electrical energy;
   a first inductor configured to generate a magnetic field for application to body tissue;
   connecting circuitry between the electric storage device and the first inductor, wherein the connecting circuitry comprises at least a first branch and a second branch;
   a switch, wherein the switch forms part of the first branch, wherein the switch is configured to electrically connect the electric storage device to the first inductor in order to enable electrical current to flow through the first branch and through the first inductor, caused by the electrical energy stored via the electric storage device, thereby causing the first inductor to generate the magnetic field, wherein the electrical current flowing through the first branch represents a first current direction of current flow between the electric storage device and the first inductor;
   an electric component or assembly of electric components, that conducts, or is arranged to conduct, electrical current in a forward direction, wherein said electric component or assembly of electric components forms part of the second branch so as to enable electrical current to flow between the electric storage device and the first inductor through the second branch, wherein the current flow in the forward direction represents a second current direction of current flow between the electric storage device and the first inductor, the second current direction being opposite the first current direction; and
   a second inductor, wherein the second inductor forms part of either the first branch or the second branch.

2. The apparatus according to claim 1, further comprising circuitry configured to selectively bypass or short-circuit the second inductor in order to selectively vary an inductance of the branch of which the second inductor forms a part.

3. The apparatus according to claim 1, wherein an inductance of the second inductor is one of:
   discretely variable; and
   substantially continuously variable.

4. The apparatus according to claim 1, further comprising one or more further inductors forming part of the branch of which the second inductor forms a part.

5. The apparatus according to claim 4, further comprising circuitry configured to selectively bypass or short-circuit the second inductor and/or one or more of the one or more further inductors in order to selectively vary an inductance of the branch of which the second inductor forms a part.

6. The apparatus according to claim 5, wherein an inductance of the second inductor and/or of at least one of the one or more further inductors is one of:

discretely variable; and substantially continuously variable.

7. The apparatus according to claim 6, wherein the inductances of the second inductor and of the one or more further inductors are chosen such that the inductance of the branch of which the second inductor forms a part is one of:

discretely variable; and substantially continuously variable from a minimum value up to a maximum value, wherein the minimum value corresponds to an inductance of the branch of which the second inductor forms a part when the second and the further inductors are bypassed or short-circuited; and wherein the maximum value corresponds to an inductance of the branch of which the second inductor forms a part when the second and the further inductors are not bypassed and not short-circuited and the inductance of the second inductor and/or of at least one of the one or more further inductors is at a maximum.

8. The apparatus according to claim 4, wherein an inductance of the second inductor and/or of at least one of the one or more further inductors is one of:

discretely variable; and substantially continuously variable.

9. The apparatus according to claim 1, wherein the first inductor comprises at least one set of turns, wherein the first inductor is disposed within a casing connected to a conduit through which extends at least one cable configured to supply electrical power to the at least one set of turns, and wherein the second inductor is not disposed within said casing.

10. The apparatus according to claim 1, wherein the electric storage device comprises a pulse capacitor which can be charged by a charging circuit.

11. The apparatus according to claim 1, wherein the electric storage device comprises a battery.

12. A method of generating a magnetic field, the method comprising:

providing an apparatus according to claim 1;

storing electrical energy in the electric storage device;

switching the switch so as to electrically connect the electric storage device to the first inductor and thereby enable electrical current to flow through the first branch and through the first inductor, caused by the electrical energy stored via the electric storage device, thereby causing the first inductor to generate the magnetic field; and enabling electrical current to flow between the electric storage device and the first inductor through the second branch via said electric component or assembly of electric components.

13. The method according to claim 12, wherein the apparatus is operated in a pulsed manner, wherein the electrical current flowing through the first branch represents a first half pulse and wherein the electrical current flowing through the second branch represents a second half pulse, wherein a duration of the second half pulse is different from a duration of the first half pulse.

14. The method according to claim 13, further comprising selectively bypassing or short-circuiting the second inductor or varying an inductance of the second inductor, thereby selectively varying an inductance of the branch of which the second inductor forms a part.

15. The method according to claim 14, wherein selectively bypassing or short-circuiting the second inductor or varying the inductance of the second inductor comprises selectively bypassing or short-circuiting the second inductor or varying the inductance of the second inductor at one of:

during the first half pulse, during the second half pulse, and between the first half pulse and the second half pulse.

16. The method according to claim 12, further comprising bringing the first inductor into proximity with body tissue, or bringing the body tissue into proximity with the first inductor, so that the magnetic field is present in said body tissue.

17. The method according to claim 16, further comprising varying the magnetic field in the body tissue so as to generate a voltage in the body tissue or to cause a movement of charges in the body tissue.

18. The method according to claim 17, wherein the voltage or the movement of charges is sufficient to cause a neural reaction or a cellular physiological reaction.

19. An apparatus for use with a first inductor for generating a magnetic field for application to body tissue, the apparatus comprising:

an electric storage device configured to store electrical energy;

a terminal for connection to the first inductor for generating a magnetic field for application to body tissue;

connecting circuitry between the electric storage device and said terminal, wherein the connecting circuitry comprises at least a first branch and a second branch;

a switch, wherein the switch forms part of the first branch, wherein the switch is configured to electrically connect the electric storage device to said terminal so as to enable electrical current to flow through the first branch and through the first inductor via said terminal when the first inductor is connected to the apparatus via said terminal, caused by the electrical energy stored via the electric storage device, thereby causing the first inductor to generate the magnetic field, wherein the electrical current flowing through the first branch represents a first current direction of current flow between the electric storage device and said terminal;

an electric component or assembly of electric components, that conducts, or is arranged to conduct, electrical current in a forward direction, wherein said electric component or assembly of electric components forms part of the second branch so as to enable electrical current to flow between the electric storage device and the first inductor through the second branch via said terminal when the first inductor is connected to the apparatus via said terminal, wherein the current flow in the forward direction represents a second current direction of current flow between the electric storage device and the first inductor, the second current direction being opposite the first current direction; and a second inductor, wherein the second inductor forms part of either the first branch or the second branch.

* * * * *